(12) United States Patent
Roger (10) Patent No.: US 6,592,587 B1
(45) Date of Patent: Jul. 15, 2003

(54) SURGICAL SCREW AND GUIDEWIRE (75) Inventor: Gregory James Roger, Miranda (AU)

(73) Assignee: Australian Surgical Design and Manufacture PTY Limited, Miranda (AU)

(*) Notice: Subject to any disclaimer, the term of this patent is extended or adjusted under 35 U.S.C. 154(b) by 0 days.

(21) Appl. No.: 09/807,864

(22) PCT Filed: Aug. 23, 2000

(86) PCT No.: PCT/AU00/00996
§ 371 (c)(1),
(2), (4) Date: Apr. 20, 2001

(87) PCT Pub. No.: WO01/15613
PCT Pub. Date: Mar. 8, 2001

(30) Foreign Application Priority Data

Aug. 26, 1999 (AU) .................................. PQ2467

(51) Int. Cl.⁷ .................. A61B 17/56; A61B 17/58; A61F 5/00
(52) U.S. Cl. .................. 606/73; 606/60; 606/72; 606/86; 606/104; 411/378
(58) Field of Search .................. 606/73, 72, 86, 606/104; 411/374, 378

(56) References Cited

U.S. PATENT DOCUMENTS 4,856,951 A * 8/1989 Blucher et al. ............. 411/178
4,944,742 A   7/1990 Clemow et al. ............. 606/59
5,718,706 A * 2/1998 Roger ........................ 606/73

FOREIGN PATENT DOCUMENTS

| DE | 27 19 883    | 11/1978 |
| DE | 41 43 362 A1 | 1/1993  |
| EP | 0 134 514 A2 | 3/1985  |
| FR | 2 577 286    | 8/1986  |
| GB | 2 266 460 A  | 11/1993 |
| WO | 00/32125     | 6/1920  |
| WO | 93/15681     | 8/1993  |

* cited by examiner

Primary Examiner—Timothy L. Maust
Assistant Examiner—Lina R Kontos
(74) Attorney, Agent, or Firm—Nath & Associates PLLC; Gary M. Nath; Marvin C. Berkowitz (57) ABSTRACT A fastening device and method for fastening at least two objects, such as bone portions, together in a desired alignment. The fastening device includes a securing member, such as a bone screw (10), having a head (11), a shank (12), and an end region (14) distal the head (11). The device also includes a guiding means, such as guidewire (20), comprising at least an elongate member. The guidewire (20) is connected to or formed integral with the end region (14) of the securing member (10). The device and method is especially useful in circumstances where it is desirable or, in fact, crucial for the objects to be so fastened in a particular and/or specific alignment. The device is also beneficial for use in fastening together any or all portions of bone surrounding a fracture site.

32 Claims, 2 Drawing Sheets

SURGICAL SCREW AND GUIDEWIRE

FIELD OF THE INVENTION

The present invention relates generally to an apparatus and process for fastening at least two objects together. More specifically, the present invention relates to an apparatus and process for fastening at least two objects together in a desired alignment. The apparatus and process of the present invention is also particularly beneficial when used in the treatment of orthopaedic injuries requiring surgical intervention.

BACKGROUND ART

Screws, nails, pins and other securing members are widely used, alone or in combination with adhesives, cements, or the like, for fastening objects together. In the fields of carpentry, mechanics and orthopaedic surgery, to name a few, there are numerous circumstances in which it is desirable and/or crucial for objects to be so fastened in a particular and/or specific alignment. Indeed, orthopaedic procedures, such as the fixation of a ligament to a bone or the fastening of one portion of bone to another, provide clear examples of such circumstances.

Fastening one object to another with a screw can be a fairly straightforward process. However, ensuring that such objects are fastened in a specific alignment can be troublesome. There are at least two main reasons for this. First, the leading end of a screw is invariably a sharp, pointed surface designed to be capable of penetrating an object into which it is to be screwed. In the absence of some very specific means for guiding the screw, it is difficult to determine the exact angle at which the screw enters the object, and therefore, it not possible or at least difficult to ensure that such ail angle is the correct one for fastening the objects together in the required alignment.

Secondly, as the screw passes from the first object into the second, until the latter has been adequately penetrated, the screw will tend to push it relatively away from the former. While the screw will be able to hold the objects together, it will not necessarily cause them to abut one another as is generally desired. In addition, the screw may enter the second object at a different angle (albeit minimally different) to that which it entered the first, and thereby prevent the possibility of having the objects fastened together in the required specific alignment. Naturally, the screw can be withdrawn and re-screwed again. However, on the second occasion, and each occasion thereafter, the screw hole within the second object, if not the one within the first object also, will tend to enlarge. As a consequence, the screw may not be able to adequately engage with the objects, and may move around in the enlarged hole/s; it may even be more prone to setting itself free over short periods of time. These complications may be undesirable in most circumstances where at least two objects have been fastened together. The complications would be particularly undesirable, and could, in fact, be associated with significant morbidity, when arising following an orthopaedic procedure to fasten together two or more portions of bone surrounding a fracture site.

The first of these difficulties has, in many respects, been overcome in the prior art with the use of cannulated screws. Each such cannulated screw has a lumen, machined or otherwise formed about its longitudinal axis, which is capable of receiving a guidewire for guiding the screw in the appropriate direction.

The use of cannulated screws in orthopaedic surgery is well known. Generally, a guidewire is passed through the bone at the most appropriate angle for the screw. Once the guidewire is in position, the lumen of the screw is passed over the guidewire, such that the screw attains the correct orientation for advancement into the bone. The screw is then advanced the required distance, and the guidewire removed.

While cannulated screws provide a mechanism for guiding screws in the appropriate direction, such screws also create a number of new problems, which are yet to have been adequately addressed. Cannulated screws are more expensive and generally more complicated to manufacture. Lacking a central core, they are also generally weaker and more prone to breakage under pressure and fatigue loading. This is particularly relevant with resorbable screws, which already have a reduced strength compared to normal orthopaedic, screws. Further, the depth of the screw thread is limited by the wall thickness of the screw extending from the outer edge of the lumen to the outer edge of the screw's shank. Each of these problems is exaggerated in screws with very small diameters, such as those used in orthopaedic procedures involving, for example, the phalanges. To these problems should also be added the fact that the tools, which are used to drive the cannulated screws into place, such as screw drivers and Allen Keys, must, themselves, also be cannulated. This, of course, further adds to the cost of using cannulated screws and also weakens the drivers.

Kirschner wires (or "K-wires") have also been used as guiding means for cannulated screws in orthopaedic surgery. A K-wire typically has a drilling trocar tip and is capable of drilling into the bones into which the K-wire is to guide the screw. The K-wire is then normally adapted to hold in place by virtue of a friction fit. However, K-wires have limited grip and are often unable to adequately hold the portions of bone together.

Another example of a screw designed to deal with the relative separation of objects upon advancement of a screw is the Herbert screw. The Herbert screw has a thread, the pitch of which varies along its length such that the pitch is greater at the leading end of the screw than it is near the head of the screw. Herbert screws can be cannulated and, if so, have the problems of normal cannulated screws as described above. Once the leading end of the Herbert screw has penetrated the second object, the latter will be drawn relatively toward the former. This is because in order to make a full turn of the thread where the pitch is greater (ie at the leading end of the screw), the screw must be turned a greater distance than to make a full turn of the thread where the pitch is lesser (ie near the head of the screw). Rotating the screw enough for a full turn of the thread near the head of the screw may cause the second object to be pushed relatively away from the first a distance equal to the pitch near the head of the screw. At the same time, however, such rotation will only lead to a partial turn of the thread at the leading end of the screw. The next, even slight, turn of the screw will be adequate to complete a full turn of the thread at the leading edge of the screw, but only just begin the next turn of the thread near the head of the screw. Consequently, the second object is drawn relatively toward the first by a distance equal to the difference between the pitch at the leading end and the pitch near the head of the screw. The objects are, therefore, drawn relatively together rather than pushed relatively apart. A problem can arise, however, when the relative motion of the two objects is fixed in amplitude as there is a risk of overtightening and therefore thread stripping on the distal object.

Unfortunately, the design of the Herbert screw does not overcome the difficulty of ensuring that the screw enters the objects at the correct angle for their desired alignment.

The present invention addresses the problems of the prior art and is adapted to substantially increase the ease of use and functionality of appropriate apparatus for securing at least two objects together.

DESCRIPTION OF THE INVENTION

In a first aspect, the present invention is a securing member when used in conjunction with a guiding means for fastening at least two objects together, the securing member having a head, a shank, and an end region distal the head, wherein the end region is engageable with the guiding means.

In a second aspect, the present invention is a guiding means when used in conjunction with a securing member for fastening two objects together, the guiding means comprising at least an elongate member, wherein at least a portion of the elongate member is engageable with the securing member.

In a third aspect, the present invention is a fastening device for fastening at least two objects together in a desired alignment, the device including a securing member having a head, a shank, and an end region distal the head, and a guiding means comprising at least an elongate member, wherein the guiding means is connected to the end region of the securing member.

In a fourth aspect, the present invention is a fastening device for fastening at least two objects together in a desired alignment, the device including a securing member having a head, a shank, and an end region distal the head, and a guiding means comprising at least an elongate member, wherein the guiding means is integral with the end region of the securing member.

In a fifth aspect, the present invention is a process for fastening at least two objects together in a desired alignment using a securing member and a guiding means according to the invention, the process including the steps of:
  (a) forming a hole in each object and abutting the objects such that the respective holes are aligned to form a lumen through both objects;
  (b) passing the guiding means through the lumen; and
  (c) using the guiding means as a guide for the securing member, advancing the securing member through the lumen of the objects until the objects are fastened together in the desired alignment.

According to a sixth aspect, the present invention is a process for fastening at least two objects together using a securing member and a guiding means according to the invention, the process including the steps of:
  (a) bringing the at least two objects at least adjacent one another;
  (b) driving the guiding means through the at least two objects such that it at least bridges an interface between the objects;
  (c) using the guiding means as a guide to advance the securing member through the at least two objects such that it at least bridges the interface between the objects.

The device and methods according to this invention may be used in a range of circumstances involving the fastening of at least two objects together. It is especially useful in circumstances where it is desirable or, in fact, crucial for the objects to be so fastened in a particular and/or specific alignment. Indeed, the device is extremely beneficial for use in fastening together any or all portions of bone surrounding a fracture site.

Preferred embodiments disclose that the securing member is a screw having at least a head, a shank, a thread formed along at least a portion of the shank, and an end region distal the head. In an alternative embodiment, the securing member may also be other than a screw, provided that it has the capacity to fasten at least two objects together, either alone or in combination with an additional securing means, such as an adhesive or a cement.

In one embodiment, wherein the securing member is a screw, the head of the screw preferably has a greater diameter than that of the shank. The head may be flat, hemispherical or of some other shape which is most appropriate for the particular purpose for which the device is being used.

In all embodiments, the head is adapted to engage a device capable of causing the securing member to advance into the objects which it is being used to fasten together. The screw may, for example, have a drive socket concentric with the head, in the form of a groove extending across its diameter capable of receiving its counter-part in the head of a screw-driver. It may also have more than one such groove, such that the head is capable of receiving the head of a Phillips Head screw driver, or any other tool which is used to screw the screw into an object. In further preferred embodiments, the concentric drive socket may be hexagonal, and therefore, be adapted to receive, for example, an Allen key.

In an embodiment where the mode of advancing the securing member does not require a screwing action, its head should be appropriately adapted to receive the tool which it will be advanced by, as for example, the head of a nail is appropriately adapted to receive the strike of a hammer.

In a preferred embodiment, the head of the securing member has a greater diameter than that of its shank. The change in diameter may arise as a sudden drop in size, wherein a side elevation of the securing member reveals the formation of a step between the head and the shank. However, the change in diameter may also be gradual, wherein the side elevation of the securing member reveals a slow tapering from the greater diameter of the head to the smaller diameter of the shank. In an alternative embodiment, the diameter of the head and that of the shank may remain the same along the length of the securing member, but the diameter may also vary along the length of the securing member depending on the purpose for which the device is being used.

It is additionally preferred that the shank has a thread formed along at least a portion of its length. In one embodiment, the thread call be formed along the entirety of the shank. Where the securing member is a bone screw, the screw may be sharp threaded and have an outermost cutting line. Where the screw is to pass by or engage soft tissue, the thread, in longitudinal section along its entirety, can be devoid of an outermost cutting thread line; for example, the thread can be approximately or wholly sinusoidal in longitudinal section so as to present a "soft" thread.

The pitch of the thread may in one embodiment vary along the shank. In a preferred embodiment, however, the pitch of the thread is fixed.

In yet a further embodiment, the securing member has an end region distal its head. The end region may, itself, be adapted to receive a guiding means or may be connected to, or integral with, such a guiding means. This feature provides an important advancement over the prior art. In particular it dispenses with the need to cannulate both the securing member and tool for advancing the securing member. Indeed, as previously explained, such cannulation is necessary in corresponding prior art devices, in order to accommodate the guiding means.

In an embodiment where the end region of the securing member is adapted to engage a guiding means, there are a variety of alternatives for enabling such engagement. In one embodiment, for example, a simple receptacle, such as a hollow cylindrical socket having a first outer and a second inner end, may be formed at the.end region of the securing member in alignment with a longitudinal axis of the shank. Accordingly, an area into which a guiding means, such as a guidewire, may be press-fit is provided. Alternative shapes for the receptacle according to this embodiment can be envisaged. Indeed, provided that a guiding means can be press-fitted into the receptacle, any shape is appropriate.

In another preferred embodiment, a hollow socket formed at the end region of the securing member in accordance with that just described may additionally be threaded so that a portion of the guiding means may be screwed into the end region of the securing member. In such an embodiment, the thread may extend along the entire length of the socket, or may take-up only a portion of the length of the socket. In the case of the latter, the guiding means may be engaged with the securing member by a combination of press-fitting and screwing.

In an alternative embodiment, methods such as adhering, cementing, welding or other forms of joining, may also be used alternatively from, or in addition to, the above for engaging or connecting the guiding means to the securing member. Note that while in some circumstances it may be desirable for, or irrelevant whether, the guiding leans remains engaged or connected with the securing member for all unlimited period, in other circumstances it may be desirable and important that the guiding means be removably engageable with the securing member. In an orthopaedic procedure to bring at least two portions of bone together around a fracture site, for example, the guiding means is used only for the purpose of guiding the securing member into place, and is preferably removed prior to closure of the surgical incision.

As previously explained, the guiding means according to this invention is used to guide the securing member in the appropriate direction to achieve fixation of the objects to be fastened in a desired alignment. In a preferred embodiment, the guiding means comprises an elongate member having a first and a second end, wherein at least a portion of the elongate member comprises an engaging portion adapted to engage the securing member. In one embodiment, the elongate member can comprise a guidewire, such as a K-wire.

In a further preferred embodiment, the first end of the guiding means is the portion which is adapted to engage the securing member. There is no reason, however, why the second end cannot be so adapted; nor, for that matter, why both ends cannot be adapted to engage the securing member. Indeed, with respect to such engagement, if it is more convenient for the guiding means according to this invention to be produced so that its first and second ends can have an interchangeable purpose, then the guiding means should be produced as such.

In all alternative embodiment, the portion of the guiding means, which is adapted to engage the securing member is intermediate the ends of the elongate member. In this embodiment, the guiding means may need to be folded, prior to engagement with the securing member, such that the portion which is adapted to engage the securing member becomes all end, or all appropriate shape, for successful engagement. By the same token, the end region of the securing member which is adapted to engage the guiding means may, itself, well be adapted so that a guiding means with all engaging portion intermediate its ends is not required to be folded for such engagement.

In a preferred embodiment, the engaging portion of the guiding means is constructed to ensure suitable engagement with the end region of the securing member. Where a cylindrical socket is formed at the end region of the securing member, the materials and construction of at least the engaging portion of the guiding means may be, such that they are amenable to being press-fit into the securing member's socket.

Similarly, where the securing member's socket has a thread along at least a portion of its length, the engaging portion of the guiding means may have a complementary thread, so that the two can be screwed together. An alternative to having a complementary thread on the engaging portion of the guiding means is to form said engaging portion from a deformable material, such as a polymeric material. In the case of the latter, the action of screwing or forcefully advancing the engaging portion into the securing member's socket may cause the cutting line of the socket's thread to cut a groove or thread into the engaging portion of the guiding means. In fact, where a complementary thread was caused to be cut into the engaging portion of the guiding means, it may be necessary (or preferred) to unscrew the guiding means from the securing member in order to separate one from the other.

In a further embodiment, the guiding means may have an additional thread formed along at least a portion of the elongate member; such an additional thread being unrelated to the guiding means' ability to engage the securing member. The thread of the guiding means, in longitudinal section along its entirety, can be devoid of an outermost cutting line. The thread can be, for example, approximately or wholly sinusoidal in longitudinal section so as to present a "soft" thread. Alternatively, the thread of the guiding means may have a sharp threadform. The profile of the threadform on the guiding means is, however, preferably relatively low compared to that of the securing member. Where the device is to be used in bone, the low profile is useful in avoiding stripping of bone which will be used by the thread on the securing member to secure the object.

Such an additional thread for the guiding means may have a number of advantages. In the first instance, this thread could provide a mechanism for securing the position of the guiding means with each progression of its advancement into the objects which are to be fastened together. Secondly, as the securing member is advanced into the objects, such an additional thread on the guiding means provides a mechanism to draw the two objects relatively together in the desired alignment. This is advantageous as once the securing member has been screwed through the first object, until it has adequately protruded into the second object, it will tend to push said second object relatively away from the first object. Accordingly, there is a risk that while the objects will be fastened to one another by virtue of the securing member connecting them, they will not necessarily abut one another (and, therefore, be fastened together) as is desired. However, provided that the guiding means and securing member are engaged; provided that such engagement ensures that the guiding means is rotated as the securing member is rotated for advancement into the objects; and provided that the pitch of the thread on the guiding means is greater than the pitch of the thread on the securing member, then the guiding means will draw the second object relatively towards the first: while with each turn, the securing member pushes the second object relatively away from the first by a distance of its pitch length, the guiding means does not extend the full length of its pitch distance into the second object, because it must be rotated further to advance that far. Consequently, the two objects are drawn relatively toward one another, and will be brought to abut one another, therefore being fastened together as is desired.

In an alternative embodiment, the pitch of the thread may vary along the length of the guiding means. In a further embodiment, where such a feature may not be required, the guiding means may be substantially smooth and, therefore, not have such an additional thread.

The present invention also discloses a process for fastening at least two objects together in a desired alignment using a securing member and a guiding means according to the invention. As disclosed in steps (a) and (b) of the fifth aspect of the invention, passing the guiding means through appropriately and purposively formed holes in each object will cause the objects to attain the desired alignment for fastening.

In embodiments wherein the guiding means is connected to, or integral with, the securing member, such as those envisaged by the third and fourth aspects of the invention, it may be necessary to insert the guiding means whilst holding onto the securing member. In another embodiment, where the guiding means is not initially engaged with the securing member, such as those envisaged by the first and second aspects of the invention, the guiding means can be passed through said holes prior to such engagement. Once the guiding means is in place, however, the securing member can then be engaged with it.

As disclosed in step (c) of the fifth aspect of the invention, the guiding means is then used to guide the securing member through the objects such that the objects are fastened together in the desired alignment. If necessary, additional or alternative securing means may also be applied in order to ensure that the securing member is capable of fastening the objects together.

The present invention has particular application in the treatment of a bone fracture requiring surgical intervention. Accordingly, in yet a further embodiment, the present invention also discloses a process for fastening at least two portions of bone together, preferably in a desired alignment, using a securing member and a guiding means according to the invention. In such an embodiment, steps (a) through (c) of the fifth aspect of the invention may be as follows:

(a) form a hole in each portion of bone, such that when the portions of bone abut one another, their respective holes line up to form a continuous lumen, the portions of bone attain a desired alignment relative to one another; then;

(b) pass the guiding means through the holes formed in each portion of bone, such that the holes are caused to line up, thereby causing the portions of bone to attain the desired alignment; and (c) use the guiding means as a guide for the securing member, advancing the securing member through the portions of bone in such a way that the portions of bone are fastened together in the desired alignment.

Where a bone fracture is being operated on in accordance with the sixth aspect, the bone portions will typically be firstly lined up and clamped before the guiding means is advanced through the bone portions. Where the guiding means comprises a threaded guidewire, it will be understood that the guidewire can be screwed through the bone portions to secure the fracture temporarily. The securing member, such as a bone screw call then be advanced through the bone portions along the path defined by the guidewire.

The additional information disclosed in relation to the discussion of a process for fastening two objects together is equally applicable to the process for fastening at least two portions of bone together. In the case of the latter, however, it is preferred that the securing member takes the form of a screw and that the guiding leans has an additional thread along its length with a pitch greater than that of the thread on the securing member.

It is additionally noteworthy that in relation to orthopaedic procedures, the device according to this invention is not limited to the repair of fracture sites requiring surgical intervention. It could also be used, among other things, as a support for ligament fixation. The invention is, therefore, applicable to a range of orthopaedic and other surgical procedures.

BRIEF DESCRIPTION OF THE DRAWINGS

By way of example, preferred embodiments of the invention are described with reference to the accompanying drawings in which.

PREFERRED MODE OF CARRYING OUT THE INVENTION

Figure 1:
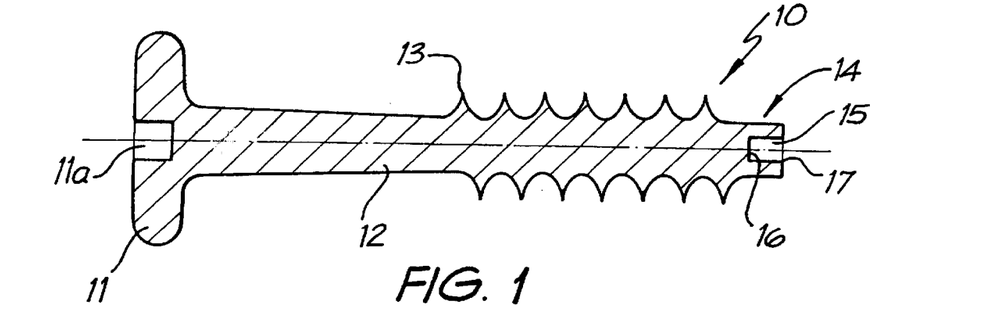
FIG. 1 is a cross-sectional view of one embodiment of a bone screw according to the present invention.

The bone screw 10 depicted in FIG. 1 is a screw having at least a head 11, a shank 12, a sharp thread 13 formed along at least a portion of the shank 12 and an end region 14 distal the head 11. It will be appreciated that the bone screw 10 could, in another embodiment, be provided with a thread that does not have an outermost cutting line.

The head 11 is adapted to engage a device capable of causing the securing member 10 to advance into the objects which it is being used to fasten together. While all possible alternatives for this adaptation are not illustrated in the figures, the screw 10 can have a drive socket 11a concentric with the head 11, in the form of a groove extending across its diameter capable of receiving its counter-part in the head of a screw driver (not shown). It may also have more than one such groove, such that the head 11 is capable of receiving the head of a Phillips Head screw driver (not shown), or any other tool which is used to screw the screw 10 into an object. In another embodiment, the concentric drive socket may be hexagonal, and therefore, be adapted to receive, for example, an Allen key (not shown). The head 11 of the screw has a greater diameter than the shank 12. The change in diameter may arise as a sudden drop in size, wherein a side elevation of the securing member reveals the formation of a step between the head 11 and the shank 12. However, the change in diameter may also be gradual, wherein the side elevation of the screw 10 reveals a relatively gentle tapering from the greater diameter of the head 11 to the smaller diameter of the shank 12.

The pitch of the thread 13 can vary along the shank 12. However, in the depicted embodiment, the pitch of the thread 13 is fixed.

Figure 3A:
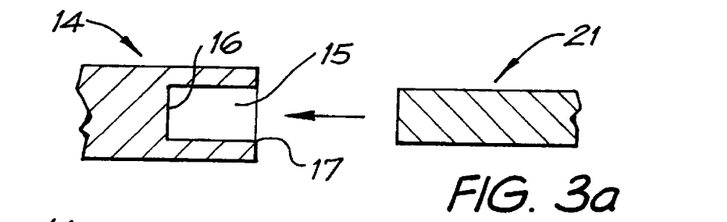
FIG. 3a is all enlarged cross-sectional view illustrating the engaging portions of both the bone screw and the guiding means according to one embodiment.

The end region 14 of the screw 10 is adapted to receive the guiding means 20 or may be connected to, or integral with, such a guiding means 20. Note that there are a variety of alternatives for enabling such engagement. In one embodiment, for example, a simple receptacle, such as a hollow cylindrical socket 15 having a first inner end 16 and a second outer end 17, may be formed at the end region 14 of the screw 10 in alignment with the longitudinal axis of the shank 12. Accordingly, an area into which a guiding means 20, such as a guidewire or K-wire, may be press-fit is provided (see FIG. 3a).

Figure 3B:
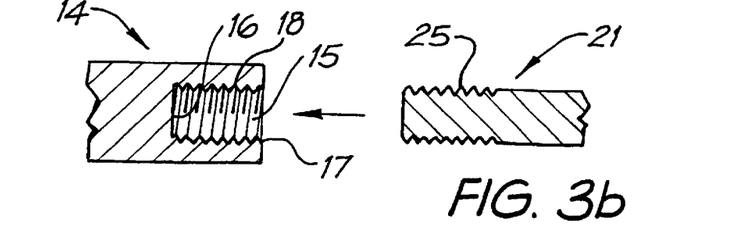
FIG. 3b is an enlarged cross-sectional view illustrating the engaging portions of both the bone screw and the guiding means according to another embodiment.
Figure 3C:
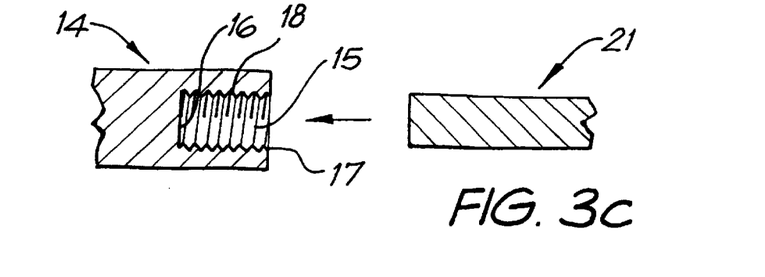
FIG. 3c is an enlarged cross-sectional view illustrating the engaging portions of both the bone screw and the guiding means according to yet another embodiment.
Figure 4:
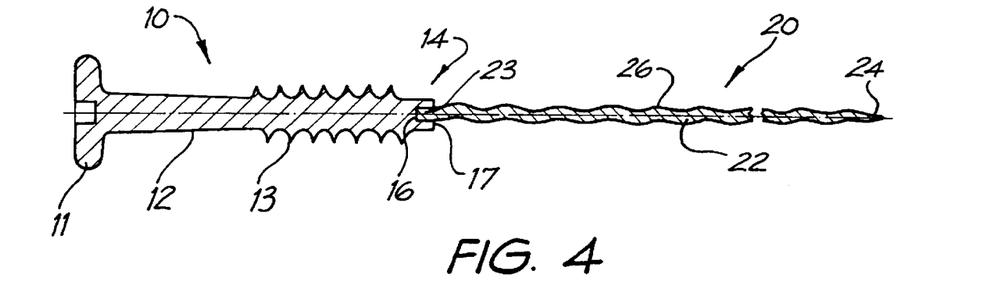
FIG. 4 is a cross-sectional view of the apparatus according to this invention, in which the guiding means and bone screw are engaged.

The hollow socket 15 formed at the end region 14 of the screw 10 in accordance with that just described may additionally have a thread 18 so that on engagement of an end portion 21 of the guiding means 20, the guiding means 20 may be screwed into the end region 14 of the screw 10. In such an embodiment, the thread 18 may extend along the entire length of the socket 15 (see both FIGS. 3b and 3c), or may take-up only a portion of the length of the socket 15. In the case of the latter, the guiding means 20 may be engaged with the screw 10 by a combination of press-fitting and screwing.

Figure 2:
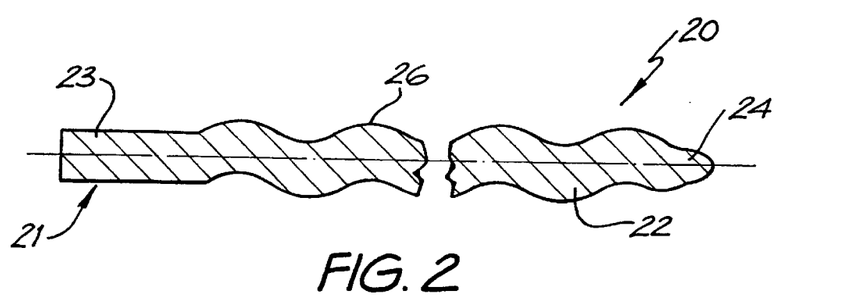
FIG. 2 is an enlarged cross-sectional view of one embodiment of a guiding means according to the present invention.

The guiding means 20 according to this invention is used to guide the screw 10 in the appropriate direction to achieve fixation of the objects to be fastened, such fixation being preferably in a desired alignment. As depicted in FIG. 2, the guiding means 20 comprises an elongate guidewire 22, having a first end 23 and a second end 24, wherein at least a portion 21 of the guidewire 22 is adapted to engage the screw 10.

In the depicted embodiments, the engaging portion 21 is at first end 23 of the guidewire 22 and is adapted to engage the screw 10. As previously explained, there is no reason, however, why the second end 24 cannot be so adapted; nor, for that matter, why both ends 23 and 24 cannot be adapted to engage the screw 10. Indeed, with respect to such engagement if it is more convenient for the guidewire according to this invention to be produced so that its first and second ends 23 and 24 respectively can have an interchangeable purpose, then the guidewire 22 should be produced as such.

The engaging portion 21 of some preferred embodiments of the guidewire 22 is adapted to correspond to the adaptation made at the end region 14 of the screw 10. In other words, where a simple cylindrical socket 15 is formed at the end region 14 of the screw 10, the materials and construction for at least the engaging portion 21 of the guidewire 22 may be such that they are amenable to being simply press-fit into the socket 15 (see FIG. 3a). Similarly, where socket 15 has a thread 18 along at least a portion of its length, the engaging portion 21 of the guidewire 22 may have a complementary thread 25, so that the two can be screwed together (see FIG. 3b). An alternative to having a complementary thread 25 on the engaging portion 21 of the guidewire 22 in such embodiments is to form at least said engaging portion 21 from a polymeric material. In the case of the latter, the action of screwing or forcefully advancing the engaging portion 21 into the socket 15 may cause the cutting line of the thread 18 of socket 15 to cut a groove or thread into the engaging portion 21 of the guidewire 22 (see FIG. 3c). Where a complementary thread was caused to be cut into the engaging portion 21 of the guidewire 22, it may be necessary (or preferred) to unscrew the guidewire 22 from the screw 10 in order to separate one from the other.

As depicted in FIG. 2, the guidewire 22 may have an additional thread 26 formed along at least a portion thereof. The additional thread 26 has a function unrelated to the thread 25 described above. This additional thread 26 in having a low sinusoidal profile does not have an outermost cutting line. It will be appreciated that in another embodiment, the thread 26 of the guidewire 22 could have an outermost cutting line.

Such all additional thread 26 for the guidewire 22 may have a number of advantages. In the first instance, this thread 26 provides a mechanism for advancing the guidewire into a bone or other object and/or act to secure the position of the guidewire 22 with each progression of its advancement into the objects which are to be fastened together. Secondly, as the securing member 10 is advanced into the objects, such all additional thread 26 on the guidewire 22 provides a mechanism to draw the two objects relatively together in the desired alignment. As disclosed in the description of the invention above, for this to occur, the pitch of the thread 26 on the guidewire 22 should be greater than the pitch of the thread 13 on the screw 10.

Figures 5A, 5B:
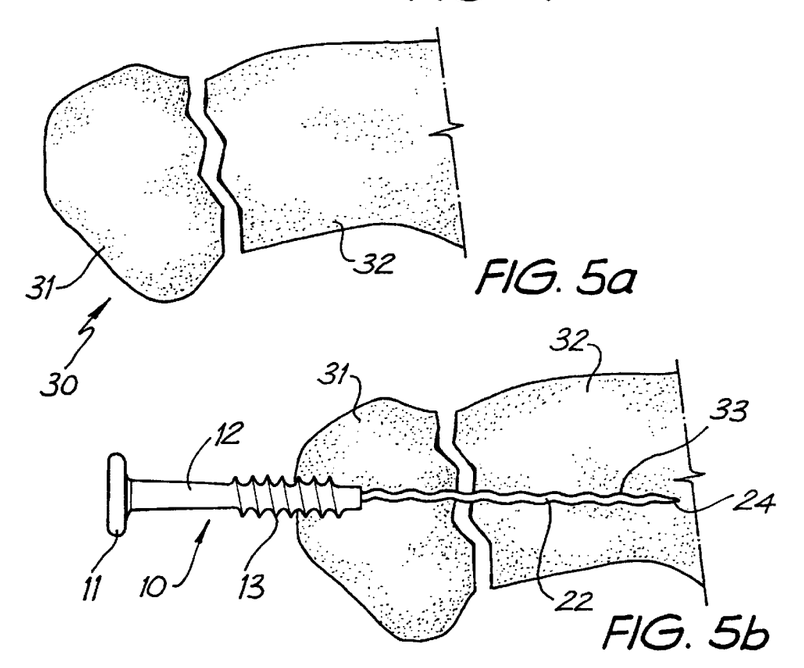
FIGS. 5a–c are cross-sectional diagrams illustrating various stages throughout the surgical repair of a fractured bone requiring such treatment.
Figure 5C:
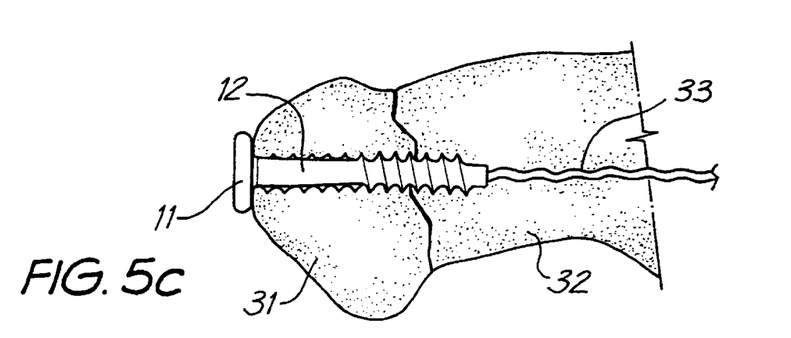

The present invention also discloses processes for fastening at least two objects together, preferably in a desired alignment, using a screw 10 and a guidewire 22 according to the invention. Indeed, in preferred embodiments, the present invention may be especially valuable in the treatment of a bone fracture requiring surgical intervention. Accordingly, also disclosed is a process for fastening at least two portions of bone together, preferably in a desired alignment, using a screw 10 and a guidewire 22 according to the invention. FIGS. 5a–c illustrate various stages throughout this process.

A bone 30 with a fracture requiring surgical intervention is shown in FIG. 5a. In one embodiment, the guidewire 22 is used to form a hole in each portion 31,32 of bone 30, such that when the portions 31,32 of bone 30 abut one another, and their respective holes line up to form a continuous lumen 33, the portions 31,32 of bone 30 attain a desired alignment relative to one another. The screw 10 is then engaged with the guidewire 22, and using the guidewire 22 as a guide, the screw 10 is advanced through the portions 31,32 of bone 30.

Having been engaged with the screw 10, the guidewire 22 is caused to rotate as the screw 10 is rotated. Because the pitch of the thread 26 on the guidewire 22 is greater than the pitch of the thread 13 on the screw 10, the two portions of bone will be drawn relatively together as the screw 10 is advanced. FIG. 5b illustrates the relationship between the guidewire 22 and the screw 10 during the process of advancing the screw 10 through the two portion of the fractured bone 30.

As shown in FIG. 5c, at the end of the procedure the two portions of bone 30 have been brought together in the desired alignment, and are fastened as such by the screw 10.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A fastening device for fastening at least two objects together in a desired alignment, the device comprising:
   a non-cannulated securing member having a head, a shank, and an end region distal the head; and
   a guidewire comprising at least an elongate member having a first end and a second end;
   wherein the first end of the elongate member is removably connectable to the end region of the securing member and extends in a direction away from the head of the securing member.

2. The fastening device of claim 1 wherein the end region includes a hollow cylindrical socket having a first outer end and a second inner end in alignment with a longitudinal axis of the shank.

3. The fastening device of claim 2 wherein the cylindrical socket is threaded so that the first end of the guidewire is screwable into the end region of the securing member.

4. The fastening device of claim 3 wherein the thread extend the entire length of the socket.

5. The fastening device of claim 1 wherein the guidewire is a K-wire.

6. The fastening device of claim 1 wherein the guidewire has a screw thread along at least a portion of its length.

7. The fastening device of claim 6 wherein the elongate member is formed from a resiliently deformable material, such as a polymeric material.

8. The fastening device of claim 6 wherein the screw thread of the guidewire, in longitudinal section along its entirety, is devoid of an outermost cutting line.

9. The fastening device of claim 8 wherein the screw thread of the guidewire is approximately or wholly sinusoidal in longitudinal section.

10. The fastening device of claim 1 wherein the securing member is a screw having a thread formed along at least a portion of the shank.

11. The fastening device of claim 10 wherein the head of the screw has a diameter greater than that of the shank.

12. The fastening device of claim 10 wherein the thread has an outermost cutting line.

13. The fastening device of claim 10 wherein the pitch of the thread is fixed.

14. A process for fastening at least two objects together in a desired alignment using a securing member and a guidewire according to claim 1, the process comprising the steps of:
   (a) forming a hole in each object and abutting the objects such that the respective holes are aligned to form a lumen through both objects;
   (b) passing the guidewire through the lumen; and
   (c) using the guidewire as a guide for the securing member, advancing the securing member through the lumen of the objects until the objects are fastened together in the desired alignment.

15. The process of claim 14 wherein the two objects are at least two portions of bone.

16. A process for fastening at least two objects together using a securing member and a guidewire according to claim 1, the process comprising the steps of:
   (a) bringing the at least two objects at least adjacent one another;
   (b) driving the guidewire through the at least two objects such that it at least bridges an interface between the objects;
   (c) using the guidewire as a guide to advance the securing member through the at least two objects such that it at least bridges the interface between the objects.

17. A fastening device for fastening at least two objects together in a desired alignment, the device comprising;
   a non-cannulated securing member having a head, a shank, and an end region distal the head; and
   a guidewire comprising at least an elongate member having a first end and a second end;
   wherein the first end of the elongate member is integrally connected with the end region of the securing member and extends in a direction away from the head of the securing member.

18. The fastening device of claim 17 wherein the securing member is a screw having a thread formed along at least a portion of the shank.

19. The fastening device of claim 18 wherein the head of the screw has a diameter greater than that of the shank.

20. The fastening device of claim 18 wherein the thread has an outermost cutting line.

21. The fastening device of claim 18 wherein the pitch of the thread is fixed.

22. A process for fastening at least two objects together in a desired alignment using a securing member and a guidewire according to claim 17, the process comprising the steps of:
   (a) forming a hole in each object and abutting the objects such that the respective holes are aligned to form a lumen through both objects;
   (b) passing the guidewire through the lumen; and
   (c) using the guidewire as a guide for the securing member, advancing the securing member through the lumen of the objects until the objects are fastened together in the desired alignment.

23. The process of claim 22 wherein the two objects are at least two portions of bone.

24. A process for fastening at least two objects together using a securing member and a guidewire according to claim 17, the process comprising the steps of:
   (a) bringing the at least two objects at least adjacent one another;
   (b) driving the guidewire through the at least two objects such that it at least bridges an interface between the objects;
   (c) using the guidewire as a guide to advance the securing member through the at least two objects such that it at least bridges the interface between the objects.

25. The fastening device of claim 17 wherein the end region includes a hollow cylindrical socket having a first outer end and a second inner end in alignment with a longitudinal axis of the shank.

26. The fastening device of claim 17 wherein the guidewire is a K-wire.

27. The fastening device of claim 17 wherein the guidewire has a screw thread along at least a portion of its length.

28. The fastening device of claim 27 wherein the elongate member is formed from a resiliently deformable material, such as a polymeric material.

29. The fastening device of claim 27 wherein the screw thread of the guide means, in longitudinal section along its entirety, is devoid of an outermost cutting line.

30. The fastening device of claim 29 wherein the screw thread of the guidewire is approximately or wholly sinusoidal in longitudinal section.

31. A fastening device for fastening at least two objects together in a desired alignment, the device comprising:

a securing member having a head, a shank, and an end region distal the head, the end region including a hollow cylindrical threaded socket having a first outer end and a second inner end in alignment with a longitudinal axis of the shank; and a guidewire comprising at least an elongate member;

wherein a portion of said guidewire may be screwed into the threaded socket of the end region of the securing member.

32. The fastening device of claim 31 wherein the thread extend the entire length of the socket.

* * * * *

UNITED STATES PATENT AND TRADEMARK OFFICE
CERTIFICATE OF CORRECTION

PATENT NO.      : 6,592,587 B1                                      Page 1 of 1
DATED           : July 15, 2003
INVENTOR(S)     : Roger It is certified that error appears in the above-identified patent and that said Letters Patent is hereby corrected as shown below:

Column 13,
Line 2, change "guide means" to -- guidewire --.

Signed and Sealed this

Twenty-first Day of October, 2003

JAMES E. ROGAN
*Director of the United States Patent and Trademark Office*